United States Patent [19]

Koobs

[11] Patent Number: 4,915,695

[45] Date of Patent: Apr. 10, 1990

[54] MULTIPLE BARREL SYRINGE

[76] Inventor: David C. Koobs, 982 West Brevard St., Apt. G6, Tallahassee, Fla. 32304

[21] Appl. No.: 242,816

[22] Filed: Sep. 12, 1988

[51] Int. Cl.$^4$ .............................................. A61M 5/18
[52] U.S. Cl. ................................... 604/191; 222/137; 604/218
[58] Field of Search ................ 604/187, 191, 209–211, 604/218; 222/135, 136, 137, 94

[56] References Cited

U.S. PATENT DOCUMENTS

| | | | |
|---|---|---|---|
| 1,950,137 | 3/1934 | Dowe | 604/191 X |
| 2,168,686 | 8/1939 | Saffir | 604/191 X |
| 2,515,956 | 7/1950 | Greenberg | 604/218 X |
| 2,875,761 | 3/1959 | Helmer et al. | 604/240 |
| 3,166,221 | 1/1965 | Nielsen | 222/137 |
| 4,188,949 | 2/1980 | Antoshkiw | 604/191 |

*Primary Examiner*—Dalton L. Truluck
*Attorney, Agent, or Firm*—William M. Hobby III

[57] ABSTRACT

A multiple barrel syringe apparatus is provided for selectively dispensing fluids. A body has a plurality of pie shaped bores therein, each bore being open at one end and narrowing at the other end into separate smaller bores opening at the other end thereof. A needle cannula having a bore therethrough or a stopcock may be attached to the other end of the body over a plurality of smaller bores so that each pie-shaped bore can have a liquid therein dispensed through a single bore. A plurality of plungers are each pie shaped for fitting in one of the cylindrical body pie shaped bores and each plunger has a groove extending down one side having a plurality of ratchet teeth therein. A plurality of pawls are formed on the cylindrical body, one pawl positioned adjacent each cylindrical body pie shaped bore on one end for selectively engaging the ratchet teeth in the groove of one plunger so that each plunger can be locked in a different position.

10 Claims, 1 Drawing Sheet

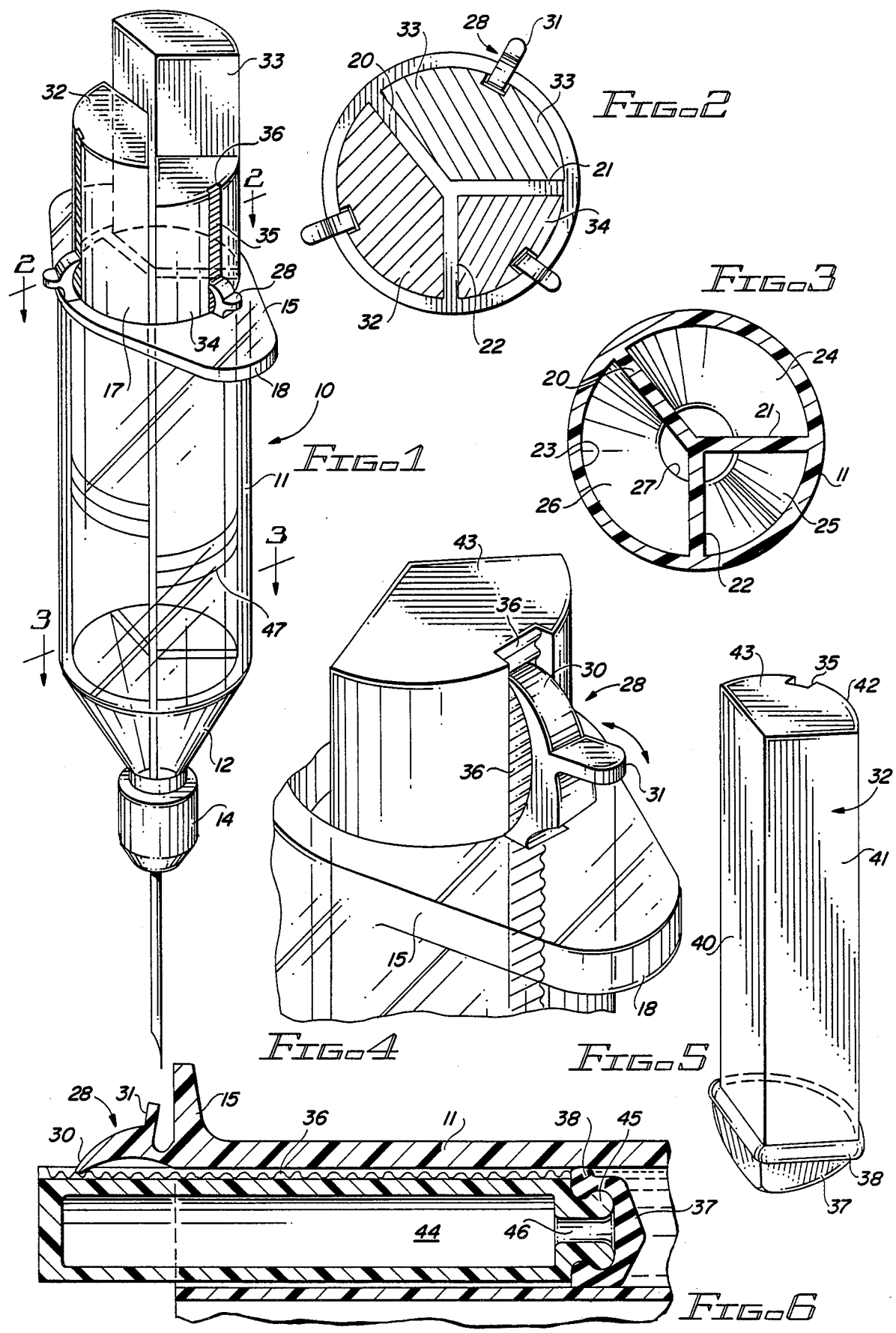

4,915,695

MULTIPLE BARREL SYRINGE

BACKGROUND OF THE INVENTION

The present invention relates to a multiple barrel syringe for selectively dispensing fluids and especially to a syringe having multiple pie shaped bores formed in one body.

Numerous types of syringe structures are available in the prior art and are operable to receive a fluid therein and mix the same by actuation of the plunger assemblies to drive all the fluids together. The plunger assemblies in different syringe techniques may be simultaneously operated to mix and dispense the fluids simultaneously or may be interconnected for independently and selectively dispensing fluids by operating one plunger at a time. The dispensing is sometimes done through a common stopcock or through a needle cannula with a single bore and it has also been accomplished through a plurality of bores in a needle cannula to avoid any mixing of the fluids being dispensed.

The present invention is directed towards a multiple barrel syringe for selected delivery of a plurality of fluids through a single needle but is formed in one cylindrical body having bores therein with pie shaped cross sections along with plungers having a similar shape with each plunger sized to fit one of the bores and each plunger having a groove extending along one elongated side with a plurality of ratchet teeth formed therein. The plunger is held and guided into position by the pie shaped cross section with the elongated groove and teeth always aligned in the same position so that a pawl formed adjacent each syringe bore is positioned adjacent the plunger groove with a blade adapted to engage the teeth formed in the groove. Each plunger can be locked into position against movement in one or both directions. Prior Patents which use multiple barrel syringes or dispensers can be seen in the Kozam et al U.S. Pat. No. 4,381,778 for a multiple barrel syringe body having a pair of cylindrical plungers inserted into separate cylindrical bores formed in the syringe body. The Kozam et al U.S. Pat. No. 4,109,653, operates in a similar manner but with formed grips for the syringe and plungers. The Kozam et al U.S. Pat. No. 4,367,737, shows a multiple barrel syringe also having a body having two cylindrical bores and individual cylindrical plungers operating in each bore.

In the Devaney et al U.S. Pat. No. 4,121,739 a dispenser for dispensing viscous fluids, such as adhesives, is provided with a unitary plunger and seal construction for driving separate plungers and separate cylindrical bores for mixing and dispensing adhesive components. In the Cucchiara U.S. Pat. No. 3,749,084, a sequentially dispensing syringe has multiple needle assemblies and has each plunger concentrically mounted in the main body and through the other plungers. Each bore is cylindrical except each bore in the body except the center bore is an annular bore driven by an annular plunger. In the Redl et al U.S. Pat. No. 4,359,049, an adhesive dispenser has a pair of syringes connected together for injection into a common dispensing needle.

An aim of the present invention is to provide a multi barrel syringe showing different size barrels which can be preloaded and locked against movement of the plungers but which can be held in a conventional manner and one or more fluids injected in any desired sequence.

SUMMARY OF THE INVENTION

The present invention relates to a multiple barrel syringe for selectively dispensing a fluid and includes a body having a plurality of bores therein having a pie shaped cross section. Each body pie shaped bore is open at one end and narrows at the other into separate smaller bores opening at the other end thereof. A needle cannula or stopcock having a single bore therethrough is attached to the other end over the plurality of smaller bores so that fluid in the pie shaped bores can be driven through the needle bore. A plurality of plungers each has a pie shaped cross section shaped to fit into one of the pie shaped bores of the body and each plunger has an elongated groove along one edge thereof having a plurality of ratchet teeth formed therein. A plurality of pawls are formed on the body and positioned adjacent each body pie shaped bore for selectively engaging the ratchet teeth in the groove on the adjacent plunger so that a plunger can be locked in place. Each pawl has a handle formed thereon for disengaging the pawl for operating the plunger. Each plunger can be of a different size to match a different size bore in the body for injecting different amounts of different fluids. The body is formed with an expanded flange around the one open end for a user to hold the syringe and each plunger may have a pie shaped resilient seal on one end and a pushing surface on the other end thereof.

BRIEF DESCRIPTION OF THE DRAWINGS

Other objects, features and advantages of the present invention will be apparent from the written description and the drawings in which:

FIG. 1 is a perspective view of a multi-barrel syringe in accordance with the present invention;

FIG. 2 is a sectional view taken on line 2—2, of FIG. 1;

FIG. 3 is a sectional view taken on line 3—3, of FIG. 1;

FIG. 4 is an enlarged sectional view of the ratchet and pawl portion of the syringe of FIG. 1;

FIG. 5 is a perspective view of a plunger; and

FIG. 6 is a sectional view of a portion of the syringe of FIG. 1 showing the ratchet and pawl mechanism.

DESCRIPTION OF THE PREFERRED EMBODIMENT

Referring to FIGS. 1 through 6 of the drawings, a multi-barrel syringe 10 has a cylindrical body 11 with a truncated cone shaped portion 12 extending from the bottom thereof forming into a smaller cylindrical shaped portion 13 having a needle 14 attached thereto. The needle cannula (or stopcock) has a bore extending therethrough. The body 11 also has a flange 15 extending around the open end 17 which flange may have a finger flange extension 18 on two sides thereof. The cylindrical body 11 has a plurality of walls 20, 21 and 22 formed therein to form three pie shaped bores 23, 24 and 25. Each bore is pie-shaped in cross-section and may be of a different size from the other bores. It will of course be clear that any size bore desired can be utilized without departing from the spirit and scope of the invention. The bottom of each bore has an angled surface 26 feeding into a smaller bore 27 which small bores are connected to the needle 14 for feeding into the single bore of the needle. It will be clear that a stopcock may also be connected to the end of the syringe without departing from the scope of the invention. A plurality of locking pawls 28 are formed as part of the housing 11 or may be separately attached as desired and each has a locking blade 30 and a releasing handle 31.

A plunger 32 is of a general pie shaped cross section and shaped to fit into the bore 26 while a plunger 33 has the same shape as the plunger 32 except sized to fit into the bore 24 and a plunger 34 is again shaped like the plungers 32 and 33 but shaped to fit into the smaller bore 25. Each of the plungers 32 has an elongated groove 35 extending along one edge and each groove has a plurality of ratchet teeth 36 formed therein which are engaged by the blade 30 of the pawl 28. Each plunger 32, as seen in FIG. 5, has a resilient rubber seal 37 formed on one end and may include an enlarged sealing surface 38 therearound. The seal is also pie shaped and overlaps the bottom of the groove 35 to prevent escape of fluid through the groove 35. Each plunger 32, 33 or 34 has a pair of angled walls 40 and 41 and an arcuate wall 42 to form a pie section but also has a pushing top surface 43. The pushing top surface may also have an extending flange to provide a better grip for the thumb to push in a particular plunger. Each plunger 32, 33 and 34 has a hollow interior 44 with a shaped end 45 for receiving the seal 37 thereover and may have an opening 46 therein which is sealed by the seal 37.

In operation the syringe may be preloaded with different injectable fluids in each bore 24, 25 and 26 and each plunger can be preinserted to the desired position and each one in a different position as shown in FIG. 1. Each plunger can be locked in place by the blade 30 of the pawl 28 engaging the ratchet teeth 36. In operation each plunger can be pushed singularly in sequence by merely unlocking the ratchet and pawl mechanism by pushing the handle 31 and driving the plunger in. The pawl mechanism may also allow the plunger to be pushed in only one direction and as illustrated the plunger can be pulled but cannot be pushed into the syringe until the handle 31 is pushed to pull the blade 30 out of engagement with the teeth 36. Different amounts of a fluid are injected from each bore because each bore is not only of a different size but may have the plunger positioned at a different position as illustrated in FIG. 1. Each bore may also have separate gradations 47 thereon for indicating the amount of fluid being injected by each plunger.

The present invention advantageously has a single cylindrical body having a plurality of bores, each holding a plunger in position for engagement with a ratchet and pawl mechanism. However, the present invention is not to be construed as limited to the form shown which are to be considered illustrative rather than restrictive.

I claim:

1. A multiple barrel syringe for selective dispensing of fluids comprising:

a body having a plurality of pie shaped bores therein, said body pie shaped bores being open at one end and narrowing at the other end into separate smaller bore opening at the other end thereof and said smaller bores converging together into one bore;

a plurality of plungers, each plunger being adapted to fit into one said pie shaped bore of said body and each plunger having a plurality of ratchet teeth thereon, each of said plurality of plungers having a pie shaped cross-section matching said pie shaped bore in said body and a pie shaped resilient seal on the end thereof;

a plurality of pawls formed on said body, one pawl positioned adjacent each body pie shaped bore one end for selectively engaging said ratchet teeth on the adjacent plunger whereby a plurality of fluids each of different amounts can be injected from the same syringe.

2. A multiple barrel syringe for selective dispensing of fluids in accordance with claim 1 in which said body has a flange around said one end thereof.

3. A multiple barrel syringe for selective dispensing of fluids in accordance with claim 2 in which said body has a generally cylindrical shaped main body portion.

4. A multiple barrel syringe for selective dispensing of fluids in accordance with claim 2 in which said body has a flange around said one end thereof having two sides thereof extending to form two finger grips for holding said body when using said syringe.

5. A multiple barrel syringe for selective dispensing of fluids in accordance with claim in which said plurality of pawls are formed as part of said body.

6. A multiple barrel syringe for selective dispensing of fluids in accordance with claim 5 in which said plurality of pawls each have a teeth engaging blade and a releasing handle formed thereon.

7. A multiple barrel syringe for selective dispensing of fluids in accordance with claim 1 in which each of said plurality bores in said body pie shaped bores has a different sized cross-section matching one said pie shaped plunger.

8. A multiple barrel syringe for selective dispensing of fluids in accordance with claim 1 in which each of said plurality of plungers is hollow and has a pushing surface on one end thereof and a resilient seal on the other end thereof.

9. A multiple barrel syringe for selective dispensing of fluids in accordance with claim 1 in which each of said plurality of plungers has a groove extending down one edge thereof and has a plurality of teeth formed in said groove for engagement with said pawl.

10. A multiple barrel syringe for selective dispensing of fluids in accordance with claim 1 in which said cylindrical body is a hollow body having at least three walls therein to form at least three angled bores therethrough, said walls being separated each from the other to form at least two bores having a different size.

* * * * *